United States Patent [19]

Kuenn et al.

[11] Patent Number: 4,764,418
[45] Date of Patent: Aug. 16, 1988

[54] VIRUCIDAL TISSUE PRODUCTS CONTAINING WATER-SOLUBLE HUMECTANTS

[75] Inventors: Cary K. Kuenn, Appleton; Daniel S. Westbrook, Green Bay, both of Wis.

[73] Assignee: Kimberly-Clark Corporation, Neenah, Wis.

[21] Appl. No.: 835,017

[22] Filed: Feb. 28, 1986

[51] Int. Cl.$^4$ ............................................. B32B 27/00
[52] U.S. Cl. .................................... 428/284; 428/290; 428/913
[58] Field of Search ............... 428/152, 153, 154, 195, 428/198, 211, 290, 284, 913

[56] References Cited

U.S. PATENT DOCUMENTS 3,227,614  1/1966  Scheuer .................................. 167/84
3,305,392  2/1967  Britt ...................................... 117/154

FOREIGN PATENT DOCUMENTS 932936   9/1973  Canada ................................. 28/0.53
2538238 12/1982  France .
1424692  2/1976  United Kingdom .

Primary Examiner—James J. Bell
Attorney, Agent, or Firm—Gregory E. Croft

[57] ABSTRACT

The tactile properties of virucidal tissue products containing carboxylic acids are improved by the incorporation of a water-soluble humectant, such as polyethylene glycol.

14 Claims, 1 Drawing Sheet

VIRUCIDAL TISSUE PRODUCTS CONTAINING WATER-SOLUBLE HUMECTANTS

BACKGROUND OF THE INVENTION

Virucidally effective facial tissues are now well known in the tissue industry. The most significant example of such a tissue is described in copending application Ser. No. 447,581 filed Dec. 13, 1982 in the names of Shafi Hossain and Kenneth Smith (herein incorporated by reference). A foreign counterpart to that application issued in Canada on June 4, 1985, as Canadian Patent No. 1,188,225 and is assigned to Kimberly-Clark Corporation.

The abovesaid application and patent describe, among other things, a tissue product containing a virucidally effective amount of certain carboxylic acids, particularly including citric acid and malic acid. Upon carrying out further research and development on this product an unusual and unexpected property was discovered. In particular, it was discovered that in some instances the perceived softness of the product decreased with aging. Although the decrease in softness appears to be linked to the relationship between the moisture level in the tissue and the presence of carboxylic acid moieties, the mechanism is not clearly understood. As a result of this discovery, considerable effort has been focused on overcoming this tendency, since perceived softness is a major factor in consumer acceptance of any tissue product.

SUMMARY OF THE INVENTION

In one aspect, the invention resides in a virucidal tissue product comprising at least one air dry cellulosic web containing one or more carboxylic acids and a water-soluble humectant. The water-soluble humectant is preferably a polyglycol such as polyethylene glycol or polypropylene glycol.

In another aspect, the invention resides in a method for making a tissue product base sheet comprising: (a) blending a water-soluble humectant with a carboxylic acid-containing virucidal composition at a temperature sufficiently high to solubilize the blend without degrading the carboxylic acid; (b) applying the solubilized blend to the surface of a cellulosic web; and (c) cooling the web to reduce the tackiness of the solubilized blend.

For purposes herein, the term "humectant" means a hygroscopic compound or material which has an affinity for water and acts to stabilize the moisture content of a cellulosic web in the presence of fluctuating humidity. The term "water-soluble" means having a Hydrophile-Lipophile Balance (HLB) number of 7 or greater. The HLB index is well known in the chemical arts and is a scale which measures the balance between the hydrophilic and lipophilic solution tendencies of a compound. The HLB scale ranges from 1 to approximately 50, with the lower numbers representing highly lipophilic tendencies and the higher numbers representing highly hydrophilic tendencies. It has been discovered that the presence of a water-soluble humectant can inhibit age-induced reduction in softness in webs containing carboxylic acids, particularly under conditions of low humidity (less than 35% relative humidity) as are encountered within the home in the wintertime in the northern climates or in very dry climates such as the southwestern United States. While not being bound to any particular theory, it is believed that the hygroscopicity of the water-soluble humectants of this invention serves to attract and retain moisture in the web. This moisture, in turn, prevents the carboxylic acid bond-forming reaction that creates a stiff web. In addition, when the water-soluble humectant is used instead of water as a vehicle for applying the virucidal composition to the tissue web, it also provides a processing advantage in that the need for drying the treated tissue is eliminated. This provides an economic processing advantage by reducing energy and equipment costs. Furthermore, it has also been found that the water-soluble humectants of this invention provide sensory advantages in their own right, such as imparting a lotioned surface feel to the web.

The water-soluble humectant can be any such material or compound which can be applied to the tissue web in a uniform manner, as by spraying, coating, dipping or printing, etc., and which possesses hygroscopic or humectant properties and which will not interfere with the virucidal effectiveness of the tissue product to the extent that the tissue product is no longer virucidally effective. It must be pointed out that many lotion-type tissue additives, which have HLB numbers less than 7 and hence are not water-soluble, interfere with virucidal activity. Examples of suitable water-soluble humectants include: polyglycols (as hereinafter defined), propylene glycol, sorbitol, lactic acid, sodium lactate, glycerol, and ethoxylated castor oil.

Polyglycols, which for purposes herein include esters or ethers of polyglycols, having a weight average molecular weight of from about 75 to about 90,000 are suitable for purposes of this invention. This molecular weight range represents physical states ranging from a low viscosity liquid to a soft wax to a fairly hard solid. The higher molecular weight polyglycols naturally have to be melted in order to be applied to a tissue web. Examples of suitable polyglycols include polyethylene glycol, polypropylene glycol, polyoxypropylene adducts of glycerol, methoxypolyethylene glycol, polyethylene glycol ethers of sorbitol, polyethylene glycol ethers of glycerol, polyethylene glycol ethers of stearic acid, polyethylene glycol ethers of lauryl alcohol, citric acid fatty esters, malic acid fatty esters, polyethylene glycol ethers of oleyl alcohol, and ethoxylated stearate esters of sorbitol. Polyethylene glycol is a preferred polyglycol because it can be applied to the tissue in amounts which are effective in improving softness without leaving a noticeable residue on the consumer's hands. Polypropylene glycol is also effective, but tends to leave more of a residue at equivalent amounts and is more hydrophobic than polyethylene glycol.

The amount of water-soluble humectant in a single ply or web of a tissue product of this invention can be about 0.05 to weight percent or greater. The weight percentage amount can vary greatly, depending upon the desired tactile properties, the amount of carboxylic acid present that needs to be counteracted, the properties of the water-soluble humectant itself, etc. At water-soluble humectant levels greater than about 20 weight percent, the tissue product becomes soggy and unacceptable for normal tissue usage. More preferably, the amount of polyglycol in a single ply or web of a tissue product can be from about 2 to about 6 weight percent. Also for purposes herein, "tissue products" are those paper products comprising one or more creped cellulosic webs or plies. Cellulosic webs suitable for use in the product of this invention include those webs useful for facial tissues, bathroom tissues, table napkins and paper towels. This includes webs having basis weights of from about 5 to about 30 pounds per 2880 square feet. It also includes webs containing a substantial proportion of synthetic fibers as well as webs which are substantially solely made of cellulose papermaking fibers.

The term "air dry" is used in its ordinary sense with respect to water content and is used to distinguish the tissue products of this invention from wet wipes, which are either individually packaged or packaged in a reclosable container. The air dry facial tissue webs of this invention typically have a moisture content of from about 1 to about 15 weight percent. The high moisture content is due to the presence of the carboxylic acids, which tend to absorb moisture from the air when humidity is high. However, without the presence of a humectant, tissue products containing carboxylic acids also give up the absorbed moisture under conditions of low humidity.

The carboxylic acid component of the product of this invention can be any carboxylic acid having the structure R-COOH, wherein R is a radical selected from the group consisting of lower alkyl, substituted lower alkyl, carboxy lower alkyl, carboxyhydroxy lower alkyl, carboxy halo lower alkyl, carboxy dihydroxy lower alkyl, dicarboxyhydroxy lower alkyl, lower alkenyl, carboxy lower alkenyl, dicarboxy lower alkenyl, phenyl, and substituted phenyl radicals. The term "lower" refers to an acid where "R" contains from one to six carbon atoms. The term "substituted" means that one or more hydrogen atoms are substituted by halogen atoms, hydroxyl groups, amino groups, thiol groups, nitro groups, cyano groups, and the like. Preferred acids are citric acid and malic acid because of their safety, efficacy, low cost and availability. All of the abovesaid carboxylic acids are deemed to have virucidal activity.

The carboxylic acids can be present in the tissue product in any amount which is virucidally effective. The term "virucidally effective amount" means an amount sufficient to cause a 2 log drop in rhinovirus type 16 within 20 minutes in accordance with the Virucidal Assay Test described in the abovesaid copending application Ser. No. 447,581 and Canadian Patent No. 1,188,225. On a weight basis, a suitable amount of carboxylic acid present in a single cellulosic web or ply of a tissue product can be from about 3% to about 50%, preferably from about 5% to about 31%, and most preferably from about 7% to about 13%. This amount will be virucidally effective and is likely to cause a decrease in the softness of the web upon aging in conditions of low humidity. Naturally, the weight percent amount of carboxylic acid in any given tissue product will depend on the number of plies or webs in the tissue product and the number of plies or webs which are treated.

DETAILED DESCRIPTION OF THE DRAWINGS

Figure 1:
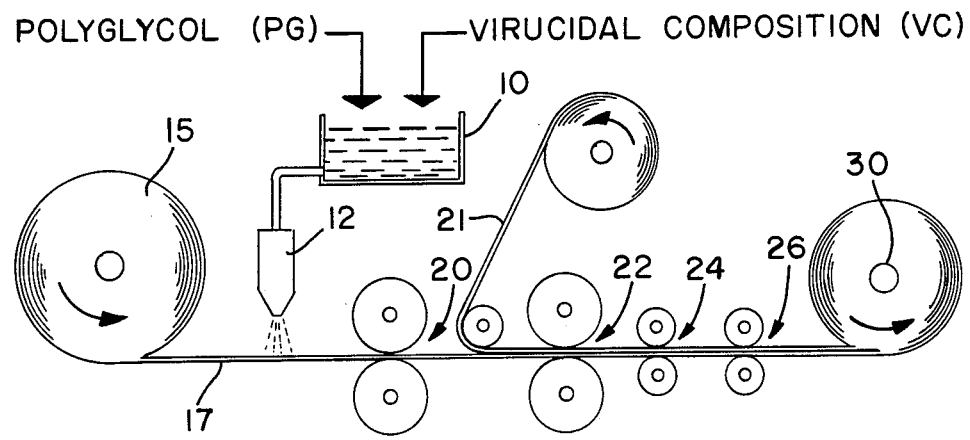
FIG. 1 is a block flow diagram illustrating a method of making the tissue products of this invention.

Referring to FIG. 1, the method of making a tissue product of this invention will be described in greater detail. Generally, the method simply provides for applying a water-soluble humectant, such as a polyglycol, as by spraying or printing, to the surface of a web containing a virucidal composition comprising at least one carboxylic acid. Advantageously, the carboxylic acid-containing virucidal composition can be premixed with the water-soluble humectant and applied at the same time.

As an example, FIG. 1 illustrates a treatment of a creped tissue base sheet in accordance with this invention. Shown is a mixing tank 10 which is filled with a mixture of a polyglycol and a suitable virucidal composition. A preferred virucidal composition contains citric acid, malic acid, and sodium lauryl sulfate in a weight ratio of 10:5:2. The virucidal composition is blended with polyethylene glycol at a weight ratio of from about 80:20 to about 5:95, respectively. A preferred blend contains, on a weight basis, 41.2% citric acid, 20.6% malic acid, 8.2% sodium lauryl sulfate, and 30% polyethylene glycol. The molecular weight of the polyethylene glycol will determine the blend temperature suitable for blending the virucidal composition with the polyethylene glycol as hereinafter described. Weight average molecular weights ranging from 400 to 1450 have been used successfully.* The contents of the mixing tank are agitated at a temperature of at least about 100° C. in order to solubilize the citric acid, malic acid and sodium lauryl sulfate. The temperature in general should not exceed about 150° C., however, in order to avoid degradation of the carboxylic acids. In the case of virucidal compositions containing malic acid, the temperature should not exceed 125° C. The lower and upper temperature limits will naturally depend upon the particular polyglycol and virucidal composition being dissolved.

*Dow Chemical Company, Polyglycol E400 and E1450.

The solubilized mixture of the virucidal composition in polyethylene glycol is transferred from the mixing tank to an application means, such as a hot melt spray nozzle 12. A roll 15 of a creped tissue base sheet 17, having a basis weight of about 9 pounds per 2,880 square feet, is unwound and passed below the spray nozzle where it is sprayed with the solubilized mixture. The degree of add-on of the solubilized mixture depends upon the virucidal effectiveness of the virucidal composition and the proportion of polyethylene glycol. For the virucidal composition described above, an add-on of about 10 weight percent is preferred. However, this amount can be about 5% or greater.

After the web has been treated, it is preferably cooled to avoid subsequent sticking after being wound up on the reel. The sticking is due to the tacky properties of the mixture of polyethylene glycol and the virucidal composition at elevated temperatures. Therefore the treated web is preferably cooled, as by passing it through a nip between two cooling rolls 20 which lower the temperature to about 40° C. or less. Thereafter the cooled web can be combined with one or more other webs 21, which can be treated or untreated, and passed through calender rolls 22 to increase smoothness and softness. The combined webs are then passed between crimp rolls 24, slitter rolls 36, and wound up on a reel 30 for subsequent converting using methods well known in the papermaking industry.

Using this simple method of treating a single tissue ply, a variety of tissue product forms can be made using combinations of plies which have been treated with a mixture of a water-soluble humectant and a carboxylic acid-containing virucidal compositon or a water-soluble humectant alone. Means for combining multiple plies, treated or untreated, are well known in the papermaking industry. It must be pointed out that although it is advantageous to combine the water-soluble humectant with the carboxylic acid-containing virucidal composition, and apply both components to the cellulosic web as a mixture, each component can also be applied to the cellulosic web separately. An advantage of applying both components as a mixture, however, is that the mixture does not readily migrate through the tissue from one surface to the other as does an aqueous virucidal solution. This permits concentrating the mixture at a particular location within the tissue product.

FIG. 2 illustrates a number of different product configurations which are possible by applying the virucidal composition and the water-soluble humectant in various locations of the tissue product. Although only two- and three-ply products are illustrated, single-ply and other multi-ply product forms are also within the scope of this invention.

Figure 2A:
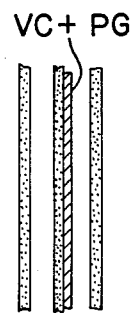
FIGS. 2A-F show different embodiments of the tissue product of this invention, illustrating different placements of the carboxylic acid-containing virucidal composition and the water-soluble humectant, which in these embodiments is a polyglycol.

FIG. 2A shows a three-ply tissue product in which the two outer plies or webs are untreated creped cellulosic webs and the center ply has been treated with a mixture of polyglycol (PG) and a carboxylic acid-containing virucidal composition (VC). The advantage of this product configuration is that the virucidal composition is confined to the center of the product and hence does not contact and possibly sensitize the user's skin.

Figure 2B:
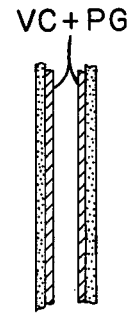

FIG. 2B shows a two-ply tissue product in which the inner surface of each ply has been treated with a mixture of polyglycol and a carboxylic acid-containing virucidal compositon. The advantage of this product form is that a single ply can be treated with the mixture and converted into a tissue product having the treated surfaces on the inside. The treatment and converting processes are relatively straight-forward.

Figure 2C:
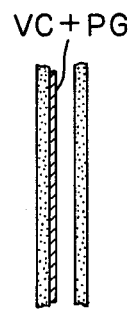

FIG. 2C shows a two-ply tissue product in which the inner surface of only one of the plies has been treated with a mixture of polyglycol and a carboxylic acid-containing virucidal composition. This product form may be the most economical to manufacture.

Figure 2D:
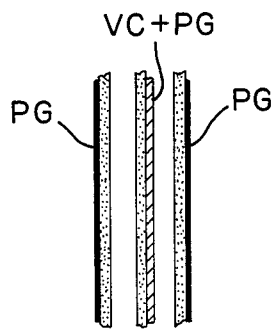

FIG. 2D shows a three-ply tissue product in which the outer surface of each of the two outer plies is treated with a polyglycol and the inner ply is treated with a mixture of polyglycol and a carboxylic acid-containing virucidal composition. The advantages of this product form are that the treated center ply is soft (less stiff) and virucidal, thereby contributing to the overall softness of the product; and that the polyglycol by itself on the outer surfaces of the outer plies imparts a soothing, lubricating sensation.

Figure 2E:
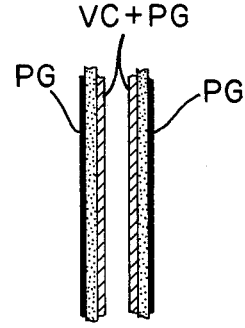

FIG. 2E shows a two-ply tissue product in which both plies have been treated on the inside with a mixture of polyglycol and a carboxylic acid-containing virucidal composition. Both plies have also been treated on the outside with polyglycol. This product form has the advantage of having the polyglycol on the outside and the virucide on the inside and provides efficiency in manufacturing and converting since both plies are identical.

Figure 2F:
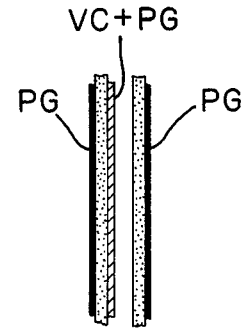

FIG. 2F shows a two-ply tissue product, similar to that shown in FIG. 2E, in which the outer surface of both plies has been treated with polyglycol and the inner surface of one of the plies has been treated with a mixture of a polyglycol and a carboxylic acid-containing virucidal composition.

As previously mentioned, it has been found that the presence of a polyglycol not only improves the softness of a tissue web which has been treated with a carboxylic acid-containing virucidal composition, but it also does not retard the virucidal efficacy of the virucidal composition. This unique combination of attributes makes polyglycol an extremely useful component for virucidal tissue products.

The foregoing drawing figures, shown for purposes of illustration, are not to be construed as limiting the scope of this invention, which is defined by the following claims.

We claim:

1. A tissue product comprising at least one air dry cellulosic web containing a water-soluble humectant and one or more carboxylic acids.

2. The tissue product of claim 1 wherein the water-soluble humectant is polyethylene glycol.

3. The tissue product of claim 1 wherein the water-soluble humectant is polypropylene glycol.

4. The tissue product of claim 1 wherein the water-soluble humectant is glycerol.

5. The tissue product of claim 1 wherein the amount of water-soluble humectant is at least about 0.05 weight percent.

6. The tissue product of claim 1 wherein the amount of water-soluble humectant is from about 0.05 to about 20 weight percent.

7. The tissue product of claim 1 wherein the amount of water-soluble humectant is from about 2 to about 6 weight percent.

8. The tissue product of claim 1 consisting of three plies, wherein the outer plies are untreated.

9. The tissue product of claim 1 consisting of two plies, wherein both plies contain a water-soluble humectant and carboxylic acid.

10. The tissue product of claim 1 consisting of two plies, wherein only one ply contains a water-soluble humectant and carboxylic acid.

11. The tissue product of claim 1 consisting of three plies, wherein the inner ply contains a water-soluble humectant and carboxylic acid and wherein the outer plies contain a water-soluble humectant.

12. The tissue product of claim 1 consisting of two plies, wherein each ply contains a water-soluble humectant and carboxylic acid on its inner surface and a water-soluble humectant on its outer surface.

13. The tissue product of claim 1 consisting of two plies, wherein each ply contains a water-soluble humectant on its outer surface and only one ply contains a water-soluble humectant and carboxylic acid on its inner surface.

14. A tissue product comprising an air dry cellulosic web containing a mixture of from about 2 to about 6 weight percent polyethylene glycol and from about 7 to about 13 weight percent of a virucidal composition comprising citric acid, malic acid, and sodium lauryl sulfate.

* * * * *